US009505694B2

(12) United States Patent
Nieuwhof et al.

(10) Patent No.: US 9,505,694 B2
(45) Date of Patent: Nov. 29, 2016

(54) PROCESS FOR THE PURIFICATION OF A LIQUID FEED COMPRISING MCA AND DCA

(71) Applicants: Melle Rinze Nieuwhof, Dieren (NL);
Cornelis Kooijman, Deventer (NL);
Willem Koelewijn, Zwolle (NL);
Hendrik Jan Vos, Apeldoorn (NL);
Lars Magnus Tollin, Skoghall (SE);
Henricus Johannes Marinus Petrus Van Hal, Barneveld (NL)

(72) Inventors: Melle Rinze Nieuwhof, Dieren (NL);
Cornelis Kooijman, Deventer (NL);
Willem Koelewijn, Zwolle (NL);
Hendrik Jan Vos, Apeldoorn (NL);
Lars Magnus Tollin, Skoghall (SE);
Henricus Johannes Marinus Petrus Van Hal, Barneveld (NL)

(73) Assignee: Akzo Nobel Chemicals International B.V., Amersfoort (NL)

( * ) Notice: Subject to any disclaimer, the term of this patent is extended or adjusted under 35 U.S.C. 154(b) by 0 days.

(21) Appl. No.: 14/351,313

(22) PCT Filed: Oct. 17, 2012

(86) PCT No.: PCT/EP2012/070523
§ 371 (c)(1),
(2) Date: Apr. 11, 2014

(87) PCT Pub. No.: WO2013/057125
PCT Pub. Date: Apr. 25, 2013

(65) Prior Publication Data
US 2014/0275625 A1 Sep. 18, 2014

(30) Foreign Application Priority Data
Oct. 20, 2011 (EP) .................. 11185948

(51) Int. Cl.
C07C 51/377 (2006.01)
C07C 51/487 (2006.01)

(52) U.S. Cl.
CPC ........... C07C 51/377 (2013.01); C07C 51/487 (2013.01)

(58) Field of Classification Search
CPC .................................. C07C 51/377
USPC ..................................... 562/604
See application file for complete search history.

(56) References Cited

U.S. PATENT DOCUMENTS

| 2,539,238 | A | 1/1951 | Eaker |
| 2,671,803 | A | 3/1952 | Sennewald et al. |
| 2,863,917 | A | 12/1958 | Rucker et al. |
| 3,754,029 | A | 8/1973 | Freyer et al. |
| 4,051,019 | A | 9/1977 | Johnson |
| 4,159,785 | A | 7/1979 | Berry, Jr. |
| 4,636,353 | A | 1/1987 | Seon et al. |
| 5,191,118 | A | 3/1993 | Correia et al. |
| 5,356,850 | A | 10/1994 | Correia et al. |
| 5,414,116 | A | 5/1995 | Correia |
| 5,449,501 | A | 9/1995 | Luebke et al. |
| 5,466,650 | A | 11/1995 | Correia |
| 5,758,699 | A | 6/1998 | Haquet et al. |

FOREIGN PATENT DOCUMENTS

| CN | 101528657 | | 9/2012 | |
| DE | 1 072 980 | | 1/1960 | |
| DE | 1 816 931 | | 7/1970 | |
| DE | 43 27 872 | | 3/1994 | |
| EP | 0 453 690 | | 10/1991 | |
| EP | 0 557 169 | | 8/1993 | |
| EP | 0 727 250 | | 8/1996 | |
| EP | 0 728 730 | | 8/1996 | |
| EP | 0 769 462 | | 4/1997 | |
| EP | 1451136 | | 1/2004 | |
| GB | 1 249 718 | | 10/1971 | |
| GB | 1 411 214 | | 10/1975 | |
| JP | 2003-144921 | | 5/2003 | |
| JP | 2008-183558 | | 8/2008 | |
| NL | 109769 | | 10/1964 | |
| NL | 109769 C | * | 10/1964 | .......... C07C 51/363 |
| RU | 2301331 | | 6/2007 | |
| RU | 2 318 796 | | 9/2009 | |
| RU | 2391331 | | 2/2010 | |
| WO | 2008/025758 | | 3/2008 | |
| WO | WO 2008025758 A1 | * | 3/2008 | |
| WO | 2008/109671 | | 9/2008 | |

OTHER PUBLICATIONS

Gaetan, Mary et al., "Trickle-Bed Laboratory Reactors for Kinetic Studies", International Journal of Chemical Reactor Engineering, 2009, vol. 7, pp. 1-68.
Shah, Y.T., Gas liquid solid reactor design, McGraw-Hill, Inc. 1979, p. 93.

(Continued)

Primary Examiner — Yong Chu
(74) Attorney, Agent, or Firm — McDonnell Boehnen Hulbert & Berghoff LLP

(57) ABSTRACT

The present invention pertains to a process for the purification of a substantially water-free liquid feed comprising monochloroacetic acid, dichloroacetic acid, optionally acid chlorides, optionally anhydrides, and optionally acetic acid, which comprises the steps of (a) adding water to the liquid feed so that a liquid feed is obtained comprising between 0.01 and 5% by weight of water, based on the total weight of the liquid feed, and (b) subsequently subjecting the liquid feed obtained in step (a) to a catalytic hydrodechlorination step by contacting it with a source of hydrogen to convert the dichloroacetic acid into monochloroacetic acid in the presence of a solid heterogeneous hydrogenation catalyst comprising one or more metals of Group VIII of the Periodic Table of the Elements deposited on a carrier.

19 Claims, No Drawings

(56) References Cited

OTHER PUBLICATIONS

Westerterp & Wammes (K Roel Westerterp and Wino J.S. Wammes), "Three-phase trickle-bed reactors", Ullmann's Encyclopedia of Industrial Chemistry, Wiley-VCH Verlag GmbH & Co. KgAA, weinheim, 2013 version, pp. 1-34 (corresponds to a newer version of 2005 cited reference).
International Search Report for International Application No. PCT/EP2012/070524, mailed on Nov. 11, 2012.
International Preliminary Report on Patentability for International Application No. PCT/EP2012/070524, issued on Apr. 22, 2014.
Hofmann, Hans, "Hydrodynamics and Hydrodynamic Models of Fixed Bed Reactors," Chapter 8, in Agostino Gianetto and Peter L. Silveston (eds.), Multiphase Chemical Reactors—Theory, Design, Scale-up, Hemispere Publishing Co., 1986, p. 256-257.
European Search Report for EP Application No. 11185953.4, mailed on Apr. 5, 2012.
Saroha, Anil K. and Nigam, K.D.P., "Trickle-bed Reactros," Reviews in Chemical Engineering, 12, 3-4, 207-347, 1996.
Griffioen, Gert and Wijbrands, Michel, "Caring for Catalysts," Hydrocarbon Engineering, Jun. 2010.
DIN EN ISO 6271-1, Clear Liquids, Estimation of colour by the platinum-cobalt scale, Part 1: Visual method, ISO 6271-1:2004, Mar. 2005.
International Search Report for International Application No. PCT/EP2012/070523, mailed on Nov. 20, 2012.
International Preliminary Report on Patentability for International Application No. PCT/EP2012/070523, issued on Apr. 22, 2014.
DIN EN ISO 6271-2, Clear Liquids, Estimation of colour by the platinum-cobalt scale, Part 2: Spectrophotometric method ISO 6271-2:2004, Mar. 2005.
European Search Report for EP Application No. 11185948.4, mailed on Apr. 5, 2012.
Third Party Observations received in corresponding EP Application No. 12 775 481.0, dated on Jan. 26, 2016.
Third Party Observations received in EP Application No. 12 778 693.7, dated Jan. 26, 2016.
Sie, S.T., et al., Process Development and Scale Up: III. Scale-up and scale-down of trickle bed processes, Reviews in Chemical Engineering, 1998, vol. 14, No. 3, pp. 203-248.
Bhaskar, M., et al., Three-Phase Reactor Model to Simulate the Performance of Pilot-Plant and Industrial Trickle-Bed Reactors Sustaining Hydrotreating Reactions, Ind. Eng. Chem. Res., 2004, vol. 43, No. 21, pp. 6654-6669.

\* cited by examiner

PROCESS FOR THE PURIFICATION OF A LIQUID FEED COMPRISING MCA AND DCA

REFERENCE TO RELATED APPLICATIONS

This application is the U.S. National Phase of PCT/EP2012/070523, filed on Oct. 17, 2012, and claims the benefit of EP Application No. 11185948.4, filed on Oct. 20, 2011.

The present invention relates to a process for the purification of a liquid feed comprising monochloroacetic acid (MCA) and dichloroacetic acid (DCA).

The predominant industrial route for the production of monochloroacetic acid is by reacting acetic acid with chlorine. Such a process is commonly known and generally makes use of a reactor in which a mixture of liquid acetic acid (HAc) is reacted with chlorine under anhydrous conditions, using acetyl chloride as the catalyst. Acetyl chloride is preferably formed in-situ by the addition of e.g. acetic anhydride. In consequence, the chlorination mixture is substantially water-free (since acetyl chloride reacts vigorously with water). In the chlorination reactor, monochloroacetic acid (MCA) and gaseous HCl are formed together with by-products of which dichloroacetic acid (DCA) and trichloroacetic acid (TCA) are examples.

After the MCA-containing reaction product mixture has passed the reactor(s) and the catalyst recovery section, DCA is present in a significant amount, typically about 3-10%. To reduce the amount of DCA in the MCA, the MCA/DCA-containing product mixture is subsequently subjected to a purification process. The purification process can either be a physical separation, such as crystallization or distillation, or a chemical conversion, such as a reduction where DCA is reduced with hydrogen in the presence of a hydrogenation catalyst, e.g. a metal-based catalyst.

As the boiling points of monochloroacetic acid and dichloroacetic acid are very close (189° and 194° C., respectively), removal of DCA from MCA by distillation is expensive and uneconomical.

With crystallization, the concentration of dichloroacetic acid in a crude monochloroacetic acid feed can only be reduced by a factor of approximately 4, i.e., for example, from 3 to 0.7-0.8% by weight, with a one-stage recrystallization. Hence, for the production of pure monochloroacetic acid, the space and time requirements are considerable. Furthermore, after several crystallizations, a mother liquor remains comprising a mixture of monochloroacetic acid and dichloroacetic acid. Although this mother liquor still comprises at least 30% by weight of monochloroacetic acid, depending on the cooling conditions, it cannot be converted into a saleable product by further crystallization and has to be regarded as waste.

It is known that the concentration of dichloroacetic acid in crude monochloroacetic acid can be reduced considerably by hydrodechlorination over a heterogeneous catalyst (for example in accordance with U.S. Pat. No. 5,191,118 and U.S. Pat. No. 5,356,850).

It is advantageous to carry out the hydrodechlorination with the acids in the liquid phase (instead of in the gas phase), as this saves the energy required for the evaporation of the feed to the hydrodechlorination and it also saves significant investment costs for equipment that would be required to evaporate the feed to the hydrodechlorination reactor.

However, it was found that when a liquid feed comprising MCA, DCA, a small amount of TCA, Hac, and optionally some traces of acid anhydrides and/or acid chlorides was subjected to a hydrodechlorination step with the acids being in the liquid phase, a dark-coloured product was obtained due to the formation of aldehydes that give rise to the formation of condensation products. Further, excessive formation of aldehydes may cause fouling in the hydrodechlorination reactor and downstream equipment. It also adds to the emission to the environment of the production site.

These issues do not play a significant role in gaseous phase hydrodechlorination processes, but they form a problem in liquid phase hydrodechlorination processes. The reason for this is that the residence time of the components in the hydrogenation column is much longer in the case of a liquid phase hydrodechlorination process compared to a gaseous phase hydrodechlorination process. This will enhance the formation of colour components due to aldol condensation of aldehydes.

It is known from EP 1451136 that these aldehydes can be removed from a process stream by oxidation using a peroxycarboxylic acid such as peracetic acid. However, percarboxylic acids are potentially explosive, which means that the reaction conditions should be chosen carefully and monitored precisely in order to prevent accumulation thereof. Furthermore, if a molar excess is used compared to the aldehydes, unreacted peroxycarboxylic acid needs to be destroyed afterwards. With the use of less than an equimolar amount of peroxycarboxylic acid, the removal of aldehydes will not be complete. All in all, this process is rather complicated and requires a delicate touch.

It is therefore an object of the present invention to provide a purification process for a liquid feed obtainable from the chlorination section of a MCA plant comprising monochloroacetic acid, dichloroacetic acid, and optionally acetic acid, acid chlorides, and/or anhydrides, wherein the hydrodechlorination step yields a product with a colour equal to or lower than 300 Pt—Co units, preferably equal to or lower than 200 Pt—Co units, and more preferably equal to or lower than 150 Pt—Co units, as measured according to ISO-6271 (either the visual or the spectrophotometric method), which process is easy to implement in industrial scale MCA production processes. More specifically, said colour is determined by applying ISO-6271 to a mixture of 25 ml water and 75 ml of said product. This product, which is directly obtained from the hydrodechlorination step, is hereinafter also denoted as hydrogenation product.

As a result, the final MCA product which is obtained after distillation (i.e. the product obtained after separating light ends from the MCA product in a first distillation column and heavy ends in a second distillation column, said product hereinafter also denoted as distillation product), has a colour equal to or lower than 100 Pt—Co units, preferably equal to or lower than 50 Pt—Co units, and preferably equal to or lower than 20 Pt—Co units as measured according to ISO-6271. A colour lower than 20 Pt—Co means that the product is not coloured when considered with the human eye.

The above-mentioned colour of the product obtained from the hydrodechlorination step is determined by applying ISO-6271 to a mixture of 25 ml water and 75 ml of the said product.

It has surprisingly been found that this objective is met if a specific amount of water is added to a liquid feed comprising MCA, DCA, optionally a small amount of TCA, optionally HAc, optionally traces of acid anhydrides and/or optionally also some traces of acid chlorides, prior to the hydrodechlorination step.

More specifically, the present invention relates to a process for the purification of a substantially water-free liquid feed comprising monochloroacetic acid, dichloroacetic acid, optionally acid chlorides, optionally anhydrides, and optionally acetic acid, which comprises the steps of (a) adding water to the liquid feed so that a liquid feed is obtained comprising between 0.01 and 5% by weight of water, based on the total weight of the thus obtained liquid feed, and (b) subsequently subjecting the thus obtained liquid feed to a catalytic hydrodechlorination step by contacting it with a source of hydrogen to convert the dichloroacetic acid into monochloroacetic acid in the presence of a solid heterogeneous hydrogenation catalyst comprising one or more metals of Group VIII of the Periodic Table of the Elements deposited on a carrier.

With the process according to the present invention, the directly obtained product (also denoted as hydrogenation product, vide supra) will be a MCA-comprising product having a reduced DCA content and a Pt—Co colour, as determined according ISO-6271, that is equal to or below a value of 300, preferably equal to or below a value of 200, and more preferably equal to or below a value of 150.

It is noted that by the term "substantially water-free" is meant that the liquid feed to be purified via the process of the present invention comprises less than 0.009% by weight of water. Preferably, acid chlorides are present in said liquid feed. Due to the presence of acid chloride, the water content of said liquid feed will be zero.

For the sake of clarity, it is noted that if the liquid feed to be purified via the process of the present invention comprises acid chloride, water needs to be added in a molar excess with respect to the acid chloride, so that eventually a liquid feed is obtained comprising between 0.01 and 5% by weight of water, based on the total weight of thus obtained liquid feed.

Water can be added to the liquid feed as plain water or as an aqueous solution of, e.g., HCl, MCA, or acetic acid.

It is furthermore noted that the term "acid chlorides" as used throughout the specification preferably denotes acetyl chloride or a mixture thereof with chloroacetyl chloride and/or dichloroacetyl chloride. The term "(acid) anhydrides" as used throughout the specification preferably denotes acetic acid anhydride, optionally mixed with one or more anhydrides selected from the group consisting of acetic acid anhydride, DCA anhydride, MCA anhydride, DCA-MCA anhydride, acetic acid-MCA anhydride, and acetic acid-DCA anhydride.

The substantially water-free liquid feed to be purified via the process according to the present invention is preferably the liquid feed which is obtained (after catalyst recovery) from a section of a monochloroacetic acid production plant in which acetic acid is reacted with chlorine in the presence of a catalyst. The catalyst is preferably acetyl chloride, which may for instance be formed in situ by the addition of acetic anhydride. The feed to be subjected to the process of the present invention preferably comprises no more than 35% by weight of acid chlorides, more preferably no more than 15% by weight of acid chlorides, even more preferably no more than 5% by weight of acid chlorides, more preferably still at least 0.05% by weight of acid chlorides, and even more preferably still at least 0.01% by weight of acid chlorides, based on the total weight of said feed. Most preferably, the feed to be subjected to the process of present invention comprises no acid chlorides at all. However, in practice the feed to be subjected to the process of the present invention typically comprises at least 0.01% by weight of acid chlorides, based on the total weight of said feed.

It was found that the water content in the liquid feed to be subjected to the dehydrochlorination step (i.e. step b of the process according to the present invention) should be at least 0.01% by weight of water, based on the total weight of the liquid feed, in order to reduce the formation of coloured byproducts enough to obtain the desired product quality. It was also found that addition of too much water resulted in the formation of polymeric byproducts. This is undesired, as these polymeric byproducts will lead to yield loss and blocking of the equipment. It was found that these problems can be avoided by adding water in such an amount that the liquid feed to be subjected to the dehydrochlorination step (step (b) of the process of the present invention) comprises no more than 5% by weight of water, based on the total weight of said liquid feed. As the water added in step (a) will typically be recycled to the chlorination stage of the MCA production process together with the light ends obtained from the first distillation step as described above, the amount of water added is preferably kept as low as possible to minimize the amount of acid chlorides (acetyl chloride is used as catalyst in said chlorination) that will be destroyed due to this recycle.

The heterogeneous catalyst which is used in step (b) of the purification process according to the present invention preferably comprises between 0.1 and 3% by weight, more preferably between 0.5 and 2% by weight, based on the total weight of the heterogeneous catalyst, of one or more metals of Group VIII of the Periodic Table of the Elements. Preferably, the heterogeneous catalyst comprises ruthenium, rhodium, palladium and/or platinum. More preferably, it comprises palladium, platinum, or a combination thereof. Most preferably, it comprises palladium (Pd) and either sulfur or a sulfur compound. For example, the catalyst described in EP 0557169 or catalysts as described in EP 0453690 are suitable for use in the present process.

The one or more metals of Group VIII of the Periodic Table of the Elements are deposited on a carrier. Preferred carriers are selected from the group consisting of activated carbon, silica alumina, zirconium oxide, and titanium oxide. Activated carbon is most preferred. The carrier may comprise sulfur or sulfur-containing components (either organic or inorganic in nature).

In a preferred embodiment, the heterogeneous catalyst which is used in step (b) of the process according to the present invention is palladium on an activated carbon carrier, while sulfur or sulfur containing components such as $CS_2$ may be added to the feed.

In one embodiment, the catalyst is preferably situated in a fixed catalyst bed, with the one or more metals of the heterogenous hydrogenation catalyst preferably being deposited on particles prepared from activated carbon, silica, or alumina, said particles being in the form of irregularly shaped granules, spheres, rings, trilobes, quadrulobes, or extrudates. More preferably, said particles are in the form of extrudates, trilobes, or quadrulobes, having a diameter of between 0.5 and 5 mm, preferably 0.8 to 3 mm, and a length of between 1 to 10 mm.

The fixed bed can consist of one single bed, or may be subdivided into multiple sub-beds that are together called "the fixed catalyst bed". The catalyst bed or each sub-bed are supported by a support grid. Furthermore, a liquid distributor may be mounted above the surface of the entire catalyst bed and/or above the surface of one or more sub-beds to provide for a good liquid distribution over the diameter of said catalyst bed.

Suitable construction materials for these column internals (i.e. the support grid and the liquid distributor) include glass lined steel; tantalum and tantalum alloys, including tantalum claddings or coatings on steel or stainless steel; platinum and platinum alloys, including platinum claddings or coatings on steel or stainless steel; zirconium and zirconium alloys, including zirconium claddings or coatings on steel or stainless steel; graphite or impregnated graphite; ceramics—such as e.g. silicon carbide (SiC), zirconia ($ZrO_2$), alumina ($Al_2O_3$), glass, or quartz; acid resistant bricks; polytetrafluorethylene (PTFE); fluoropolymer—e.g. PTFE, perfluoralkoxy polymers (PFA), fluorinated ethylene-propylene (FEP) or polyethylenechlorotrifluoroethylene (ECTFE)—linings or coatings on steel, stainless steel, or fiber-reinforced plastics; nickel-chromium alloys; nickel-chromium-molybdenum alloys; nickel-copper alloys; silver, including silver claddings or silver coatings on steel or stainless steel; niobium and niobium alloys; and polyether ether ketone and PEEK-coated steel.

Preferred construction materials for the internals are glass lined steel; tantalum and tantalum alloys, including tantalum claddings or coatings on steel or stainless steel; platinum and platinum alloys, including platinum claddings or coatings on steel or stainless steel; zirconium and zirconium alloys, including zirconium claddings or coatings on steel or stainless steel; graphite or impregnated graphite; ceramics—such as silicon carbide (SiC), zirconia ($ZrO_2$), alumina ($Al_2O_3$), glass, or quartz; acid resistant bricks; polytetrafluorethylene (PTFE); fluoropolymer—e.g. PTFE, perfuloralkoxy polymers (PFA), fluorinated ethylene-propylene (FEP) or polyethylenechlorotrifluoroethylene (ECTFE)—linings or coatings on steel, stainless steel, or fiber-reinforced plastics.

More preferred construction material of the internals are glass lined steel; graphite or impregnated graphite; tantalum and tantalum alloys, including tantalum claddings or coatings on steel or stainless steel; and zirconium and zirconium alloys, including zirconium claddings or coatings on steel or stainless steel.

Most preferably, the construction material for the internals is graphite or impregnated graphite.

The source of hydrogen that is fed to the purification process according to the present invention is a source of hydrogen gas, which can either be substantially pure hydrogen gas or a gas comprising hydrogen gas and up to 50 mole % of nitrogen, hydrogen chloride, or a mixture thereof.

The liquid feed to be subjected to the catalytic hydrodehalogenation step (b) according to the present invention (i.e. the liquid feed obtained from step (a) of the process according to the present invention) preferably comprises
  (i) between 60 and 99.5% by weight of monochloroacetic acid,
  (ii) between 0.05 and 20% by weight, preferably between 1 and 12% by weight, of dichloroacetic acid,
  (iii) between 0 and 30% by weight of acetic acid,
  (iv) between 0.1 and 5% by weight of water, preferably between 0.1 and 1% by weight of water, most preferably between 0.1 and 0.5% by weight of water, and
  (v) between 0 and 5% by weight of other components,
up to a total of 100%, based on the total weight of the liquid feed.

Other components may include a minor amount of acid anhydrides, trichloroacetic acid, bromoacetic acid, and alpha-chloropropionic acid. It is noted that due to the presence of the water, acid chlorides cannot be present in said liquid feed.

The hydrodechlorination step is preferably carried out using a vertical tubular reactor containing the solid heterogeneous hydrogenation catalyst as described above in a fixed bed (also sometimes denoted as a stationary bed of catalyst particles).

However, other well established reactor types are also suited. These comprise slurry reactors, either mechanically stirred or stirred via an external slurry recycle that may also drive a venturi that sucks in the gas from the reactor headspace (as e.g. mentioned in CN 101528657), in which the catalyst is suspended in the liquid. Suitable reactor construction materials include glass lined steel; tantalum and tantalum alloys, including tantalum claddings or coatings on steel or stainless steel; platinum and platinum alloys, including platinum claddings or coatings on steel or stainless steel; zirconium and zirconium alloys, including zirconium claddings or coatings on steel or stainless steel; graphite or impregnated graphite; ceramics—e.g. silicon carbide (SiC), zirconia ($ZrO_2$), alumina ($Al_2O_3$), glass and quartz; acid resistant bricks, polytetrafluoroethylene (PTFE); fluoropolymer—e.g. PTFE, perfuloralkoxy polymers (PFA), fluorinated ethylene-propylene (FEP) or polyethylenechlorotrifluoroethylene (ECTFE)—linings or coatings on steel, stainless steel, or fiber-reinforced plastics; nickel-chromium alloys; nickel-chromium-molybdenum alloys; nickel-copper alloys; silver, including silver claddings or silver coatings on steel or stainless steel; niobium and niobium alloys; and polyether ether ketone or PEEK coated steel.

Preferred construction materials are glass lined steel; tantalum and tantalum alloys, including tantalum claddings or coatings on steel or stainless steel; platinum and platinum alloys, including platinum claddings or coatings on steel or stainless steel; zirconium and zirconium alloys, including zirconium claddings or coatings on steel or stainless steel; graphite or impregnated graphite; ceramics—such as silicon carbide (SiC), zirconia ($ZrO_2$), alumina ($Al_2O_3$), glass and quartz; acid resistant bricks; polytetrafluoroethylene (PTFE); fluoropolymer—e.g. PTFE, perfuloralkoxy polymers (PFA), fluorinated ethylene-propylene (FEP), or polyethylenechlorotrifluoroethylene (ECTFE)—linings or coatings on steel, stainless steel, or fiber-reinforced plastics.

More preferably, the construction material is selected from the group consisting of glass lined steel; tantalum and tantalum alloys, including tantalum claddings or coatings on steel or stainless steel; and zirconium and zirconium alloys, including zirconium claddings or coatings on steel or stainless steel.

The most preferred construction material is glass lined steel.

When the hydrodechlorination step is carried out using a vertical tubular reactor containing the solid heterogeneous hydrogenation catalyst as described above in a fixed bed (also sometimes denoted as a stationary bed of catalyst particles), the liquid feed to be subjected to the catalytic hydrodehalogenation step (b) according to the present invention is fed to the top of the vertical tubular reactor. The hydrogen gas or the mixture of hydrogen gas and up to 50 mole % of an inert gas is preferably fed to the top of the vertical tubular reactor (resulting in a co-current downflow with the liquid feed). The hydrogen gas or mixture of hydrogen gas and up to 50 mol % of an inert gas can also be fed from the bottom of the vertical tubular reactor (i.e. in countercurrent with the liquid feed); however, as the operating window is smaller (i.e. the capacity of the reactor is limited by flooding), the co-current downflow embodiment is preferred.

Preferably, the liquid feed to be subjected to the catalytic hydrodehalogenation step (b) according to the present invention is fed to the top of said vertical tubular reactor at a superficial mass velocity of between 1 and 10 kg/s per square meter of the horizontal cross-section of said reactor (the term superficial mass velocity ($kg/m^2/s$) refers to the mass flow divided by the horizontal cross-sectional area of said reactor). Preferably, it is fed to the top of said vertical tubular reactor at a superficial mass velocity of at least 2 kg/s per square meter of the horizontal cross-section of said reactor, more preferably at least 2.5 kg/s per square meter of the horizontal cross-section of said reactor, and most preferably at least 3 kg/s per square meter of the horizontal cross-section of said reactor. Preferably, the liquid feed is fed to the top of said vertical tubular reactor at a superficial mass velocity of at most 8 kg/s per square meter of the horizontal cross-section of said reactor, more preferably at a superficial mass velocity of at most 7 kg/s per square meter of the horizontal cross-section of said reactor, and most preferably at a superficial mass velocity of at most 6 kg/s per square meter of the horizontal cross-section of said reactor.

The source of hydrogen is fed to the top of the vertical tubular reactor at a superficial gas velocity of between 0.025 to 0.25 $Nm^3/s$ per square meter of the horizontal cross-section of the vertical tubular reactor (the term superficial gas velocity (m/s) refers to the gas velocity based on the horizontal cross-section of said vertical tubular reactor). Preferably, the source of hydrogen is fed to the top or bottom of the vertical tubular reactor at a superficial gas velocity of at least 0.03 $Nm^3/s$ per square meter of the horizontal cross-section of the vertical tubular reactor, more preferably at a superficial gas velocity of at least 0.035 $Nm^3/s$ per square meter of the horizontal cross-section of the vertical tubular reactor, and most preferably at a superficial gas velocity of at least 0.04 $Nm^3/s$ per square meter of the horizontal cross-section of the vertical tubular reactor. Preferably, it is fed at a superficial gas velocity of at most 0.25 $Nm^3/s$ per square meter of the horizontal cross-section of the vertical tubular reactor, more preferably of at most 0.20 $Nm^3/s$ per square meter of the horizontal cross-section of the vertical tubular reactor, and most preferably of at most 0.15 $Nm^3/s$ per square meter of the horizontal cross-section of the vertical tubular reactor.

The temperature in the top of the vertical tubular reactor is preferably kept between 100 and 200° C., and more preferably between 145 and 175° C. The pressure in the top of the vertical tubular reactor is preferably kept between 0.2 and 1.0 MPa, preferably between 0.3 and 0.6 MPa.

In order to minimize the risk of liquid maldistribution in the trickle bed reactor (see e.g. Saroha & Nigam, "Trickle-bed reactors," *Reviews in Chemical Engineering*, 12, 3-4, 207-347, 1996), the fixed bed wherein the heterogeneous hydrogenation catalyst is situated preferably has been prepared by loading the vertical tubular reactor with the heterogeneous hydrogenation catalyst using a dense loading technique. Maldistribution in catalyst beds is known to significantly decrease the reactor's performance and runtime. The dense loading technique is a conventional loading technique whereby the vertical tubular reactor is loaded with particles of catalyst simultaneously over the entire cross-section of said reactor. The result is that a catalyst bed is obtained which is uniformly loaded and wherein the density is increased when compared to other reactor loading techniques. When compared to sock loading, a well-known loading technique, the density of the catalyst bed has increased by on average at least 10%, as can be found in Gert Griffioen and Michel Wijbrands, "Caring for Catalysts," *Hydrocarbon Engineering*, June 2010. The fixed bed with densely loaded catalyst according to the present invention can for instance be prepared using the well-known Densicat® or the Catapac™ technique. Suitable dense loading methods and equipment are described in EP 769,462, U.S. Pat. No. 4,051,019, U.S. Pat. No. 4,159,785, EP 0727250, WO 2008/109671, and U.S. Pat. No. 5,449,501.

A typical industrial-scale MCA production plant comprises a chlorination section where liquid acetic acid is reacted with chlorine gas under anhydrous conditions using acetyl chloride as the catalyst. Gaseous HCl formed in this process is typically fed to one or more condensers in order to remove and recover organic components (such as acetyl chloride, acetic acid, monochloroacetic acid) in the HCl gas. The liquid feed obtainable from this chlorination section is typically subjected to a stripping operation using HCl gas in order to remove anhydrides and/or acid chlorides present in said feed. In the process according to the present invention, the liquid feed obtainable from the chlorination section of a MCA plant is preferably subjected to a stripping step prior to subjecting it to step (a) of the process according to the present invention, i.e. prior to the addition of water in an amount so that a liquid feed is obtained comprising between 0.01 and 5% by weight of water, based on the total weight of the thus obtained liquid feed. In a preferred embodiment, said stripping step is performed at a pressure of at least 1.6 bar, more preferably at least 1.7 bar, even more preferably at least 2 bar, more preferably at least 3 bar, and most preferably at least 4 bar. Preferably, the stripping step is performed at a pressure no higher than 10 bar, more preferably, no higher than 8 bar. The advantage of performing this stripping step under elevated pressure is that due to the higher pressure in the stripper column, more HCl will dissolve in the bottom product of the stripper column, thus preventing the formation of anhydrides from acid chlorides. As a result, the liquid feed which is subjected to dehydrochlorination step (b) comprises less anhydride or even no anhydride at all. This is an advantage as due to the presence of HCl in dehydrochlorination step (b), anhydrides would be converted into acid chlorides, which would subsequently be converted into aldehydes, leading to colour issues as explained above.

The process according to the present invention is further illustrated by the following non-limiting examples.

COMPARATIVE EXAMPLE A

The product from the chlorination comprising 76.7% monochloroacetic acid, 3.1% dichloroacetic acid, 12.1% acetic acid, 6.2% acetyl chlorides, 1.2% anhydrides, 0.7% HCl was fed to the top of an acetyl chloride stripper at a rate of 2,793 kg/h. HCl gas was fed to the bottom of the acetyl chloride stripper at a rate of 1,122 kg/h. The bottom of the acetyl chloride stripper was operated at a pressure of 5 bar(a) and a temperature of 126° C. The bottom product of the acetyl chloride stripper, comprising 85.3% monochloroacetic acid, 3.4% dichloroacetic acid, 8.6% acetic acid, 1.6% of acetyl chlorides, and 1.1% hydrogen chloride, was mixed with a gas flow of 56 $Nm^3$ hydrogen per hour. This gas-liquid was heated to a temperature of 163° C. and fed to a distributor in the top of a vertical tubular reactor. The vertical tubular reactor accommodated a fixed catalyst bed with a total catalyst inventory of 2,956 kg and a total length of 14 m. The catalyst particles were extrudates as mentioned in EP 0557169. The vertical tubular reactor was well insulated and was operated in an adiabatic mode. The gas phase leaving the reactor was partially condensed at a temperature of 40° C. and the liquid reflux was mixed with the liquid phase leaving the reactor to obtain the hydrogenation product. A sample was taken from this hydrogenation product and the Pt—Co colour was measured to be above 1,000 units on the Pt—Co scale when measured according to ISO 6271.

More specifically, this colour was determined by applying ISO-6271 to a mixture of 25 ml water and 75 ml of the said product. Visual inspection of this sample from the hydrogenation product showed a very dark liquid.

As a result, the final product after distillation (i.e. the product obtained after separating light ends from the hydrogenation product in a first distillation column (with MCA recovered at the bottom of the distillation column) and separating heavy ends in a second distillation column (with MCA recovered at the top of the distillation column), vide supra) was strongly coloured. A sample was taken from this final product and the Pt—Co colour was measured to be 600 units on the Pt—Co scale when measured according to ISO 6271. More specifically, this colour was determined by applying ISO-6271 to a mixture of 25 ml water and 75 ml of the said product.

Visual inspection of this sample from the final product showed a brown liquid.

EXAMPLE 1

The above-mentioned example was repeated. Only in this case water was pre-mixed with the bottom product of the acetyl chloride stripper (being the bottom product of the acetyl chloride stripper in Comparative Example A comprising 1.6% of acid chlorides) before the addition of hydrogen to obtain a water content of 0.7 wt %, based on the total weight of the thus obtained water-comprising liquid bottom product of the acetyl chloride stripper. In this case the Pt—Co colour of the hydrogenation product was 150 units on the Pt—Co scale when measured according to ISO 6271 (measured by applying ISO-6271 to a mixture of 25 ml water and 75 ml of said product). Visual inspection of this sample from the hydrogenation product showed a pale yellow liquid.

As a results the final product after distillation (i.e. the product obtained after separating light ends from the hydrogenation product in a first distillation column (with MCA recovered at the bottom of the distillation column) and separating heavy ends in a second distillation column (with MCA recovered at the top of the distillation column), vide supra) was colourless. A sample was taken from the final product and the Pt—Co colour was measured to be less than 20 units on the Pt—Co scale when measured according to ISO 6271 (measured by applying ISO-6271 to a mixture of 25 ml water and 75 ml of said product). Visual inspection of this sample from the final product showed a colourless liquid.

EXAMPLE 2

The product from the chlorination comprising 77.5% monochloroacetic acid, 2.4% dichloroacetic acid, 14.6% acetic acid, 4.2% acetyl chlorides, 0.3% anhydrides, and 1.0% HCl was fed to the acetyl chloride stripper at a rate of 9,800 kg/h. HCl gas was fed to the bottom of this stripper at a rate of 2,840 kg/h. However, in this case the bottom of the stripper was operated at a lower pressure of 1.6 bar (a) and at a temperature of 135° C. Less HCl will be dissolved in the bottom product from the stripper, therefore the bottom product of the stripper will contain more acid anhydrides. A sample was taken from the bottom product of the stripper and analyzed with HPLC and $^1$H-NMR for the presence of anhydrides and acid chlorides. The sample contained 87.6% monochloroacetic acid, 2.7% dichloroacetic acid, 9.2% acetic acid, 0.1% anhydrides, 0.1% acid chlorides, and 0.3% HCl. When water is added to this product from the stripper to obtain a water content of 0.4 wt %, based on the total weight of the thus obtained liquid product from the bottom of the acetyl chloride stripper, the traces of acid chlorides react vigorously with water to the corresponding acids. However, the reaction of anhydrides with water is much slower and it is difficult to reach complete conversion. A sample was taken after the addition of water and subsequently analyzed with $^1$H-NMR for the presence of anhydrides and acid chlorides. The sample contained 460 mg/kg anhydrides and no acid chlorides. The thus obtained water-comprising liquid product from the acetyl chloride stripper was mixed with 160 Nm$^3$/h hydrogen. The thus obtained gas-liquid mixture was heated to a temperature of 160° C. and fed to a distributor in the top of a vertical tubular reactor. The vertical tubular reactor accommodated a fixed catalyst bed with a total catalyst inventory of 3,580 kg and a total length of 14 m. The catalyst particles were extrudates as mentioned in EP 0557169. The vertical tubular reactor was well insulated and was operated in an adiabatic mode. The gas phase leaving the reactor was partially condensed at a temperature of 40° C. and the liquid reflux was mixed with the liquid phase leaving the reactor to obtain the hydrogenation product. The presence of anhydrides in the feed to the hydrogenation leads to the formation of aldehydes in the hydrogenation. As a result, a yellow coloured hydrogenation product is obtained. A sample is taken from the hydrogenation product and the Pt—Co colour is measured to be 300 units on the Pt—Co scale when measured according to ISO 6271. Acetaldehyde levels in the sample are above 600 mg/kg.

As a result, the final product after distillation (vide supra) shows a pale yellow colour. A sample is taken from this final product and the Pt—Co colour is measured to be 100 units on the Pt—Co scale when measured according to ISO 6271.

EXAMPLE 3

The product from the chlorination comprising 76.5% monochloroacetic acid, 3.6% dichloroacetic acid, 11.0% acetic acid, 8.1% acetyl chlorides, 0.1% anhydrides, 0.7% HCl was fed to the top of an acetyl chloride stripper at a rate of 8,720 kg/h. HCl gas was fed to the bottom of this stripper at a rate of 3,425 kg/h. The bottom of the acetyl chloride stripper was operated at an elevated pressure pressure of 3.2 bar (a) and at a temperature of 155° C. After this stripping process at elevated pressure no anhydride is present anymore and there are only traces of acid chlorides. A sample was taken from the bottom product of the stripper and analyzed with HPLC and $^1$H-NMR for the presence of anhydrides and acid chlorides. The sample contained 89.8% monochloroacetic acid, 4.2% dichloroacetic acid, 5.2% acetic acid, 0.1% acid chlorides, and 0.7% HCl. When water was added to this product from the stripper to obtain a water content of 0.35 wt % (based on the total weight of the thus obtained liquid product from the bottom of the acetyl chloride stripper), the traces of acid chlorides reacted vigorously with water to the corresponding acids. After the addition of water a sample was taken from the thus obtained water-comprising liquid product from the bottom of the acetyl chloride stripper and analyzed with $^1$H-NMR for the presence of anhydrides and acid chlorides. The sample contained no anhydrides and no acid chlorides. The thus obtained water-comprising liquid from the bottom of the acetyl chloride stripper was mixed with 200 Nm$^3$/h hydrogen. The thus obtained gas-liquid mixture was heated to a temperature of 160° C. and fed to a distributor in the top of a vertical tubular reactor. The vertical tubular reactor accommodated a fixed catalyst bed with a total catalyst inventory of 3,580 kg and a total length of 14 m. The catalyst particles were extrudates as mentioned in EP 0557169. The vertical tubular reactor was well insulated and was operated in an adiabatic mode. The gas phase leaving the reactor was partially condensed at a temperature of 40° C. and the liquid reflux was mixed with the liquid phase leaving the reactor to obtain the hydrogenation product. A pale yellow hydrogenation product was obtained. A sample was taken from the hydrogenation product and the Pt—Co colour was measured to be 120 units on the Pt—Co scale when measured according to ISO 6271.

As a result, the final product after distillation was colourless. A sample was taken from this final product and the Pt—Co colour was measured to be less than 20 units on the Pt—Co scale when measured according to ISO 6271. Visual inspection of this sample from the final product showed a colourless liquid.

The invention claimed is:

1. A process for the purification of a substantially water-free liquid feed comprising monochloroacetic acid and dichloroacetic acid to produce a hydrogenation product, which comprises the steps of
   (a) obtaining the substantially water-free liquid feed from a section of a monochloroacetic acid production plant wherein acetic acid is reacted with chlorine in the presence of a catalyst,
   (b) stripping the substantially water-free liquid feed using HCl at a pressure between 2 and 10 bar,
   (c) adding water to the substantially water-free liquid feed so that a second liquid feed is obtained comprising between 0.01 and 5% by weight of water, based on the total weight of the second liquid feed, and
   (d) subsequently subjecting the second liquid feed to a catalytic hydrodechlorination step by contacting it with a source of hydrogen to convert the dichloroacetic acid into monochloroacetic acid in the presence of a solid heterogeneous hydrogenation catalyst comprising one or more metals of Group VIII of the Periodic Table of the Elements deposited on a carrier, thus producing the hydrogenation product,
   wherein the hydrogenation product is a monochloroacetic acid-comprising product having a reduced dichloroacetic acid content and a Pt—Co color (as determined according to ISO-6271) that is equal to or below a value of 300.

2. The process according to claim 1 wherein the solid heterogeneous hydrogenation catalyst comprises between 0.1 and 3% by weight, based on the total weight of the solid heterogeneous hydrogenation catalyst, of the one or more metals of Group VIII of the Periodic Table of the Elements.

3. The process according to claim 1 wherein the solid heterogeneous hydrogenation catalyst comprises at least one of palladium and platinum.

4. The process according to claim 1 wherein the carrier is selected from the group consisting of activated carbon, silica, alumina, zirconium oxide, and titanium oxide.

5. The process according to claim 1 wherein the substantially water-free liquid feed comprises between 0.01 and 35% by weight of acid chlorides.

6. The process according to claim 1 wherein the second liquid feed comprises
   (i) between 60 and 99.5% by weight of monochloroacetic acid,
   (ii) between 0.05 and 20% by weight of dichloroacetic acid,
   (iii) between 0.1 and 30% by weight of acetic acid,
   (iv) between 0.1 and 5% by weight of water, and
   (v) between 0 and 5% by weight of other components, up to a total of 100%, based on the total weight of the second liquid feed.

7. The process according to claim 1 wherein the hydrodechlorination step is carried out using a vertical tubular reactor containing the solid hydrogenation heterogeneous catalyst.

8. The process according to claim 7 wherein the solid hydrogenation heterogeneous catalyst is situated in a fixed catalyst bed.

9. The process according to claim 8 wherein the second liquid feed is fed to the top of the vertical tubular reactor and hydrogen gas or a mixture of hydrogen gas and up to 50 mole % of an inert gas is either fed to the top or fed to the bottom of the vertical tubular reactor.

10. The process according to claim 7 wherein hydrogen gas or a mixture of hydrogen gas and up to 50 mole % of an inert gas is fed to the top of the vertical tubular reactor, the temperature in the top of the vertical tubular reactor is between 100 and 200° C. and wherein the pressure in the top of the vertical tubular reactor is between 0.2 and 1.0 MPa.

11. The process according to claim 7 wherein hydrogen gas or a mixture of hydrogen gas and up to 50 mole % of an inert gas is fed to the bottom of the vertical tubular reactor, the temperature at the top of the vertical tubular reactor is between 100 and 200° C. and wherein the pressure at the bottom of the vertical tubular reactor is between 0.2 and 1.0 MPa.

12. The process according to claim 3 wherein the carrier is selected from the group consisting of activated carbon, silica, alumina, zirconium oxide, and titanium oxide.

13. The process according to claim 4 wherein the substantially water-free liquid feed comprises between 0.01 and 35% by weight of acid chlorides.

14. The process according to claim 2 wherein the hydrodechlorination step is carried out using a vertical tubular reactor containing the solid hydrogenation heterogeneous catalyst.

15. The process according to claim 14 wherein the solid hydrogenation heterogeneous catalyst is situated in a fixed catalyst bed.

16. The process according to claim 15 wherein the second liquid feed is fed to the top of the vertical tubular reactor and hydrogen gas or a mixture of hydrogen gas and up to 50 mole % of an inert gas is either fed to the top or fed to the bottom of the vertical tubular reactor.

17. The process according to claim 14 wherein hydrogen gas or a mixture of hydrogen gas and up to 50 mole % of an inert gas is fed to the top of the vertical tubular reactor, the temperature in the top of the vertical tubular reactor is between 100 and 200° C. and wherein the pressure in the top of the vertical tubular reactor is between 0.2 and 1.0 MPa.

18. The process according to claim 1 wherein the solid heterogeneous hydrogenation catalyst comprises between 0.1 and 3% by weight, based on the total weight of the solid heterogeneous hydrogenation catalyst, of the one or more metals of Group VIII of the Periodic Table of the Elements.

19. The process according to claim 1 wherein the solid heterogeneous hydrogenation catalyst comprises at least one of palladium and platinum.

* * * * *